United States Patent [19]

Murib

[11] Patent Number: 4,626,521

[45] Date of Patent: Dec. 2, 1986

[54] SELECTIVE CATALYTIC OXIDATION OF CARBON MONOXIDE IN HYDROCARBON STREAM TO CARBON DIOXIDE

[75] Inventor: Jawad H. Murib, Cincinnati, Ohio

[73] Assignee: National Distillers and Chemical Corporation, New York, N.Y.

[21] Appl. No.: 635,337

[22] Filed: Jul. 27, 1984

Related U.S. Application Data

[60] Continuation-in-part of Ser. No. 542,321, Oct. 17, 1983, abandoned, which is a division of Ser. No. 200,242, Oct. 24, 1980, abandoned, which is a continuation of Ser. No. 929,067, Jul. 28, 1978, abandoned, which is a continuation-in-part of Ser. No. 799,812, May 23, 1977, abandoned.

[51] Int. Cl.[4] ............................................. B01J 23/58
[52] U.S. Cl. ..................................... 502/328; 502/330
[58] Field of Search ................................ 502/328, 330

[56] References Cited

U.S. PATENT DOCUMENTS

| | | | |
|---|---|---|---|
| 1,937,689 | 12/1933 | Frazer | 423/437 |
| 3,267,045 | 8/1966 | Isacks, Jr. et al. | 502/328 |
| 3,338,952 | 8/1967 | Callahan et al. | 502/328 |
| 3,529,935 | 9/1970 | Lorenz et al. | 423/437 |
| 3,839,549 | 10/1974 | Schwab | 423/437 |
| 4,025,561 | 5/1977 | Suggitt et al. | 502/328 |
| 4,314,084 | 2/1982 | Pinillos et al. | 502/328 |

OTHER PUBLICATIONS

Yao, Yung-Fang Yu, "The Oxidation of H.C. and CO Over Metal Oxides," *Journal of Catalysis*, V33, 108–122 (1974).

Primary Examiner—Andrew H. Metz
Assistant Examiner—Chung K. Pak
Attorney, Agent, or Firm—Kenneth D. Tremain

[57] ABSTRACT

A method is disclosed for selectively oxidizing carbon monoxide present in a hydrocarbon stream to carbon dioxide employing a specially prepared supported catalyst containing cobalt oxide, said catalyst being prepared by successively impregnating the support with a solution of an alkaline compound and a solution containing cobalt ions, calcining the impregnated support and washing the calcined support to activate the catalyst.

9 Claims, 4 Drawing Figures

SELECTIVE CATALYTIC OXIDATION OF CARBON MONOXIDE IN HYDROCARBON STREAM TO CARBON DIOXIDE

CROSS REFERENCE TO RELATED APPLICATIONS

This application is a continuation-in-part of copending application Ser. No. 542,321, filed Oct. 17, 1983, now abandoned, which is a division of application Ser. No. 200,242, filed Oct. 24, 1980, now abandoned, which is a continuation of application Ser. No. 929,067, filed July 28, 1978, now abandoned, which is continuation-in-part of application Ser. No. 799,812, filed May 23, 1977, now abandoned.

BACKGROUND OF THE INVENTION

This invention relates to the field of methods for catalytically oxidizing carbon monoxide to carbon dioxide, and more particularly, to methods for selectively catalytically oxidizing carbon monoxide present in a hydrocarbon stream using a specially prepared supported cobalt oxide catalyst.

Numerous synthetic routes to such products as acetic acid, acrylic acid, vinyl acetate and benzyl acetate, rely upon the catalytic oxidation of a hydrocarbon, for example, ethylene in the case of acetic acid and vinyl acetate, propylene in the case of acrylic acid, and toluene in the case of benzyl acetate. In addition to the principal reaction product, small quantities of carbon monoxide are also produced in these reactions. Following the recovery of the principal product, the reaction effluent is recycled so that any unreacted starting material can be fully utilized. It is known that carbon monoxide deactivates the catalysts, for example, palladium metal, which are commonly used for these syntheses. Accordingly, it is highly desirable that the carbon monoxide be converted to the dioxide prior to the recycling of the reaction effluent without, however, causing any significant oxidation of the unreacted hydrocarbon present in the effluent.

It is well known that cobalt oxide is a useful catalyst for the oxidation of carbon monoxide to carbon dioxide. Ismailov et al., *Azerb. Khim. Zh.*, 1969, (4), 75–80 (Russian), describes the oxidation of carbon monoxide and gaseous hydrocarbon present in a simulated internal combustion engine exhaust using a supported cobalt oxide catalyst. The maximum level of carbon monoxide conversion was 50% and was achieved at 800° C. Belgium Pat. No. 814,130 describes a cobalt aluminate catalyst useful in gas masks and as a component of cigarette filters. U.S. Pat. No. 3,839,545 describes the accelerated combustion of both carbon monoxide and hydrocarbons in exhaust gases using a catalyst containing a mixture of copper and manganese oxides and the oxides of other metals such as cobalt. The oxidation of hydrocarbons and CO is described in the article entitled "The Oxidation of Hydrocarbons and CO over Metal Oxides III. $Co_3O_4$" by Yung-Fan Yu Yao, *Journal of Catalysis*, 33, 108–122 (1974). In none of the foregoing is there a selective oxidation of carbon monoxide to the virtual exclusion of the hydrocarbon component which may be present. The catalytic oxidation of propylene is described in the article entitled "Regularities in Catalytic Properties of Metal Oxides in Propylene Oxidation" by U. Morooka and A. Ozaki, *Journal of Catalysis*, 5, 116–124 (1966). A series of experiments is discussed therein and shows that a cobalt oxide catalyst, prepared by calcining silicon carbide pellets impregnated with cobalt nitrate, readily oxidized propylene.

SUMMARY OF THE INVENTION

It has now been very surprisingly discovered that selective and substantially complete oxidation of carbon monoxide present in a hydrocarbon-containing gas can be accomplished at moderate temperatures using a supported cobalt oxide catalyst which is specially prepared in accordance with the invention.

Broadly stated, the method of this invention comprises introducing a gas containing carbon monoxide, oxygen and a hydrocarbon into an oxidation reaction zone containing a catalytically effective amount of a specially prepared supported cobalt oxide catalyst and reacting the carbon monoxide and oxygen in said reaction zone at an elevated temperature and for a period effective to provide substantially complete conversion of the carbon monoxide to carbon dioxide without causing any significant oxidation of the hydrocarbon.

In general, the supported cobalt oxide catalyst is prepared by successively impregnating the support with a solution of an alkaline compound and a solution of a cobalt compound, calcining the impregnated support and washing the calcined support with a solvent, e.g., water, to activate the catalyst.

The method of this invention is especially useful for converting the carbon monoxide present in reaction effluents resulting from the production of acetic acid, acrylic acid, vinyl acetate, allyl acetate and benzyl acetate via catalytic oxidation methods.

DETAILED DESCRIPTION OF THE INVENTION

Figure 1:
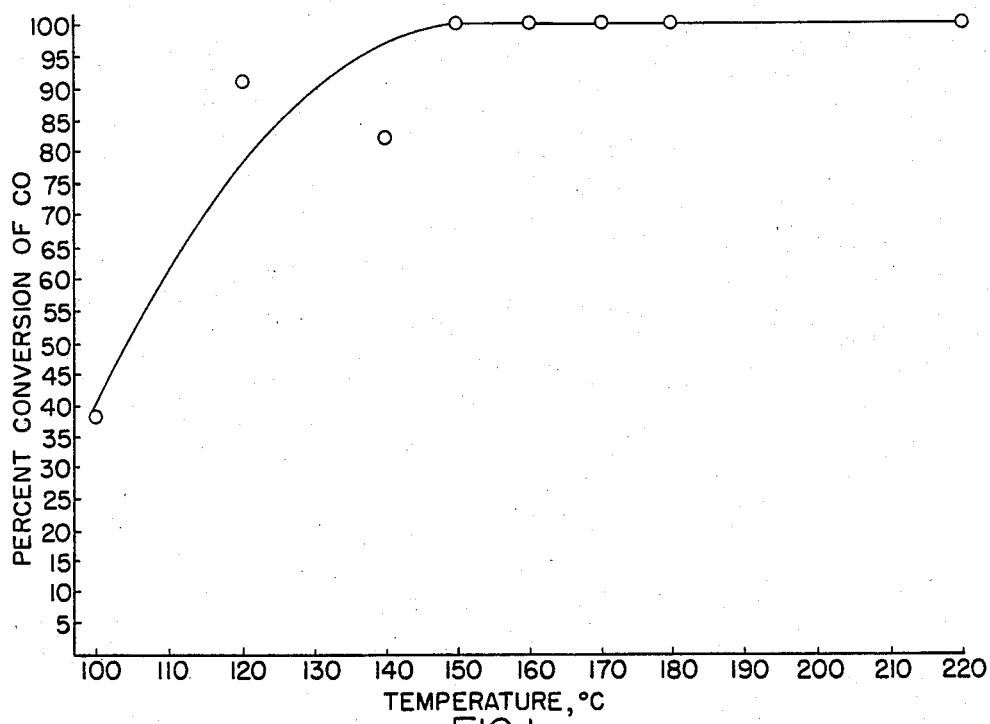
FIGS. 1–4 are graphs, based on data from Examples 4–7, respectively, showing the effect of temperature on the conversion of carbon monoxide.

The preferred support is alumina because of its demonstrated effectiveness. Silica, as shown hereinbelow, has been found to be inoperative because a feed stream containing carbon monoxide was not oxidized. It is not known why alumina provides a supported cobalt oxide catalyst having the unexpected property of selectively oxidizing carbon monoxide in a hydrocarbon containing gaseous feed stream while silica does not. However, it is considered within the scope of the invention that other support materials which provide a similar catalytic activity as alumina may also suitably be employed. Known support materials include titnania, zirconia, and the like. A highly suitable alumina is an alumina purchased from Harshaw Chemical Co. having a surface area of about 3–7 square meters/gram ($m^2/g$), an alpha alumina content >95%, a theta alumina content <5% and an apparent bulk density (packed) of about 1.07–1.17 g/ml. This is the alumina used in the examples.

The total amount of cobalt, calculated as CoO, deposited on the carrier can vary widely, e.g., from about 0.1 to about 10% by weight, and preferably, from about 0.5 to about 5% by weight of the support.

The method of preparing the supported catalyst comprises impregnating the support first with a solution of an alkaline compound and then a solution of a cobalt compound, calcining the impregnated support and washing the calcined support with a solvent, e.g., water, to activate the catalyst.

Impregnation of the support may be accomplished by known means. For example, the catalyst may be prepared by soaking the alumina with a solution of the alkaline compound and evaporating the solution while in contact with the alumina. Mixing is preferentially used to evenly distribute the deposition of the compound. Alternatively, the solution can be contacted with the alumina by passing the solution through a column containing the alumina in order to absorb the alkaline compound on the alumina. The impregnated alumina is then preferably dried, e.g. with hot air, and impregnated with a solution of the cobalt compound. After this successive impregnation, the support has thereon the alkaline compound and the cobalt compound and products of the reaction therebetween. For example, when using potassium carbonate and cobaltous chloride, the support will contain potassium carbonate, cobaltous chloride, cobaltous carbonate and potassium chloride in varying amounts depending upon the proportions of the reactants used and the impregnation conditions. It is highly preferred that the support be impregnated first with the alkaline compound because of its demonstrated effectiveness. This procedure leaves a deposit of the alkaline compound on the support which support is then impregnated with the cobalt compound.

The impregnated support is then calcined using known techniques. For example, heating in air at about 200° C. to about 800° C. for up to 48 hours to convert the cobalt containing support to cobalt oxide. Calcination in air at about 200° C. to 300° C. for about 15 to 20 hours has been found to be suitable, although calcination conditions may very widely as is known in the art.

It is an important feature of the invention that the calcined support be washed to activate the catalyst. As is shown hereinbelow a calcined catalyst which has not been washed does not oxidize any appreciable amount of the carbon monoxide even at 158° C. After the calcined catalyst is washed, however, the catalyst unexpectedly oxidizes the carbon monoxide while leaving the hydrocarbon essentially intact. Without being limited to theory, it is believed that the washing operation removes soluble salts from the catalyst which hinder the activity of the catalyst. The activity of the catalyst caused by the washing operation was totally unexpected. While water is the preferred washing agent, other suitable solvents may be employed. Water is preferred because of its low cost and accessibility. Deionized water is highly preferred because of its demonstrated effectiveness.

The calcined catalyst may be washed by contacting the catalyst with the solvent by known techniques, e.g., passing the solvent through a column containing the catalyst. The washing time may vary widely, up to about 48 hours, preferably up to about 24 hours, e.g., 5–10 hours. Ambient temperatures is suitable although higher or lower temperatures may be employed.

Alkaline compounds and cobalt compounds useful in the preparation of the catalysts of this invention are those which can be dissolved in a suitable solvent, such as water. In addition, the alkaline compound and the cobalt compound selected must be capable of reacting together to provide an insoluble cobalt compound and a soluble alkaline compound. Further, the insoluble cobalt compound produced must be capable of providing an insoluble cobalt oxide upon calcination. In this fashion, an insoluble cobalt compound is formed on the alumina support which is converted to an insoluble cobalt oxide during calcination. The subsequent water washing removes from the alumina support all the soluble compounds, i.e., any of the original alkaline and cobalt reactants remaining after the reaction and the alkaline compound produced when the insoluble cobalt compound was formed, leaving the cobalt oxide in a catalytically active condition.

Exemplary alkaline compounds useful in the catalyst preparation contain an alkali or alkaline earth metal cation and an anion selected from the group consisting of hydroxide and carbonate and include potassium carbonate, sodium hydroxide, potassium carbonate and the like. Exemplary cobalt compounds for the catalyst preparation contain anions selected from the group consisting of chloride, nitrate, and sulfate and include cobaltous chloride, cobaltous nitrate, and the like.

In preparing the catalyst, the molar ratio of the alkaline compound to the cobalt compound may vary widely. Preferably, the molar ratio of the alkaline compound to the cobalt compound is at least the stoichiometric requirement, preferably about 1 to 5 times the stoichiometric requirement. Thus, for example, when potassium carbonate and cobaltous chloride are employed, the stoichiometric requirement is 1 mole to 1 mole and the preferred molar ratio of the alkaline compound to the cobalt compound is about 1 to 5. In other instances, the stoichiometric requirement of the potassium compound to the cobalt compound may be 2 moles to 1 mole, for example, with potassium hydroxide and cobaltous chloride, thereby requiring a preferred molar ratio range of 2 to 10. A highly preferred molar ratio is about the stoichiometric requirement to about 5 times the stoichiometric requirement.

The oxygen for oxidizing the carbon monoxide can be pure oxygen, an oxygen-containing gas mixture such as air or air enriched with oxygen. The gas mixture may also contain an inert diluent gas such as carbon dioxide or nitrogen.

While stoichiometric proportions of oxygen and carbon monoxide can be used, it is advantageous to introduce into the oxidation reaction zone an excess of oxygen to assure complete conversion of the carbon monoxide to carbon dioxide.

The gaseous reaction medium will contain an amount of carbon monoxide which will vary according to the conditions under which it is produced. Typical concentration of carbon monoxide can vary from about 0.01% to about 5% by volume of gaseous medium. Similarly, the amount, and nature, of hydrocarbon present in the gaseous medium will vary according to the manner in which a particular synthesis is carried out. Among the hydrocarbons encountered herein are ethylene, propylene, toluene, and the like. The amount of hydrocarbon in the reaction medium can vary over wide limits and frequently will be from about 2 mole percent to about 25 mole percent for the aforementioned syntheses.

The reaction temperature may vary from about 100° C. to about 220° C. Generally, a temperature of about 150° C. is sufficient to oxidize substantially all of the carbon monoxide without causing any significant oxidation of the hydrocarbon. If it is desirable to operate at lower temperature, e.g., 100° C. to about 150° C., the catalyst should be prepared by impregnating the alumina with the alkaline compound and the cobalt compound wherein the molar ratio of alkaline compound to the cobalt compound is greater than the stoichiometric requirement, e.g., up to about 5 times the stoichiometric requirement.

The reaction pressure may vary over a wide range,

Examples 2 to 7 are illustrative of the method of this invention of selectively converting the carbon monoxide in a recycle stream containing propylene.

Effect of Carbon Monoxide on Catalyst Performance

Catalyst: 0.3% Pd, 0.5% Au, 27.4% $H_3PO_4$
Support: Pittsburgh Activated Carbon BPL
Feed: 5% $C_3H_6$, 10.4% $O_2$, 39.3% $N_2$, 45.3% $H_2O$
Reaction Conditions: 45 psia, 2.5 sec residence time

| Temp. °C. | Vol. % Carbon Monoxide Total Feed | Space Time Yield g Acrylic Acid/hr/l Catalyst | % $C_3H_6$ Conversion | % Selectivity Acrylic Acid | % Selectivity Carbon Dioxide | % Selectivity Carbon Monoxide |
|---|---|---|---|---|---|---|
| 200 | 0 | 37 | 15 | 64 | 11 | 3 |
| 200 | 1.0 | 26 | 12 | 58 | 12 | — |
| 200 | 0 | 31 | 14 | 59 | 8 | 2.4 |
| 225 | 0 | 51 | 22 | 60 | 11 | 7 |
| 225 | 0.5 | 41 | 20 | 59 | 14 | 8 |
| 225 | 1.1 | 42 | 18 | 55 | 15 | 5 |
| 225 | 1.8 | 33 | 16 | 52 | 16 | 8 |
| 225 | 0 | 39 | 18 | 58 | 11 | 6 |
| 225 | 0.3 | 37 | 15 | 63 | 12 | 3 |
| 225 | 0.3 | 35 | 16 | 58 | 12 | 3 |
| 225 | 0.3 | 38 | 16 | 61 | 11 | 5 |

The percent selectivity was calculated on the basis of the propylene reacted. It is significant that the selectivity ratios were not grossly altered by the presence of carbon monoxide. The data show that the presence of carbon monoxide in the feed did affect the conversion rate of propylene in a substantial way.

e.g., up to 200 psig, or higher. Preferably pressures of about atmospheric to 50 psig are employed to minimize equipment cost.

It is an additional feature of the invention that the catalyst may be used to remove carbon monoxide from a hydrocarbon containing gas without the use of oxygen or other oxidizing agent. An ethylene gas stream containing trace amounts of carbon monoxide is exemplary. It is highly advantageous to remove the carbon monoxide from such a stream and the catalyst of the invention may be suitably employed for such a purpose by contacting the stream with the catalyst and the carbon monoxide being oxidized to carbon dioxide by the catalyst itself. This will, of course, require periodic regeneration of the catalyst. A preferred continuous process could utilize a dual flow catalytic contact system. Thus, the hydrocarbon containing gas is caused to flow through the catalyst in one tube until the catalyst is "deactivated" and then the hydrocarbon containing gas is caused to flow through another tube containing "active" catalyst while the former tube is being regenerated.

Residence time of the carbon monoxide/hydrocarbon-containing reaction medium in the oxidation reaction zone can also vary widely, from 1 to 120 seconds generally being sufficient for substantially complete conversion, the optimum residence time depending, of course, on carbon monoxide and oxygen concentration, and the amount and nature of the cobalt oxide catalyst.

The activity of the catalyst can be readily monitored by the mere expediency of analyzing the effluent to determine to $CO/CO_2$ ratio thereof, or alternatively absolute amounts of CO or $CO_2$. Such determination can be effected by art-recognized methods as by vapor phase chromatography or similar techniques. Thus, nearly spent catalyst can be replaced with fresh catalyst when the carbon monoxide values exceed predetermined limits.

Example 1 which follows demonstrates the deleterious effect of the presence of carbon monoxide on a catalyst system used for the oxidation of propylene to acrylic acid.

EXAMPLE 2

Preparation and Use of Catalyst Without Washing

Alumina pellets (35.15 g) of an average size of ⅛"×⅛" were impregnated by soaking in 20 ml of an aqueous solution containing 0.55 g $K_2CO_3$. 1 ½ $H_2O$. Following drying in hot air, the pellets were impregnated by soaking with 20 ml of an aqueous solution containing 2.16 g $CoCl_2.6H_2O$. The mole ratio of $K_2CO_3:CoCl_2=0.4$. The resulting impregnated pellets were calcined in air at 230° C. for 17 hours. The catalyst was transferred into a reaction zone maintained at about 158° C. and atmospheric pressure and contacted with a gaseous feed containing, in mole %, 18.6% $O_2$, 0.77% CO, 69.9% $N_2$, 6.1% propylene and the balance He. The outlet gas contained 0.75% CO, showing no appreciable oxidation of the CO. The amount of propylene was about 5.3%; this amount was determined by difference and consequently, this difference is within experimental error and does not indicate if any propylene was oxidized.

Use of Catalyst After Washing

The above catalyst was removed from the reaction zone and washed with deionized water for 15 hours, dried and reloaded into the reaction zone. The reaction zone was maintained at about 158° C. and contacted with a gaseous feed containing, in mole %, 18.9% $O_2$, 0.81% CO, 70.9% $N_2$, 4.8% propylene (by difference) and the balance He. The outlet gas contained 0.25% CO (69% reduction) and 5.50% propylene and shows that CO was now selectively oxidized by the washed catalyst as compared to the unwashed catalyst.

Similar experiments with an $SiO_2$ support showed no CO oxidation of the gaseous feed either before or after washing.

EXAMPLE 3

Alumina pellets (176 gram (g)) of an average size of ⅛"×⅛" were impregnated by soaking with an aqueous solution containing 4.9 grams $K_2CO_3.1$ ½ $H_2O$ dissolved in 100 ml of deionized water. Following drying, the pellets were impregnated with a 100 ml aqueous solution containing 3.95 grams of $CoCl_2.6H_2O$ and the resulting impregnated pellets were calcined at 230° C. to 300° C. in air for 42 hours to provide a cobalt oxide supported catalyst. The mole ratio of $K_2CO_3$:$CoCl_2=1.79$. The catalyst was thereafter washed with deionized water for about 7 hours at ambient temperature to remove any soluble salt and dried in hot air. An effluent obtained from the palladium metal catalyzed oxidation of propylene to acrylic acid, containing, inter alia, an average of 0.5 mole percent of CO, 5 mole percent of unreacted propylene, 12 mole percent of oxygen and 82 mole percent of nitrogen, was introduced into a reaction zone containing 85 grams of the cobalt oxide catalyst. Substantially complete conversion of CO to $CO_2$ was effected in the reaction zone after a single pass of the effluent at 190° to 200° C. and 54 psig. Residence time of the effluent in the reaction zone was about 3 to 5 seconds. No measurable loss of propylene was detected.

EXAMPLE 4

Alumina pellets (35.15 g) were impregnated by soaking in 20 ml of an aqueous (deionized $H_2O$) solution containing 0.55 g (3.33 mM) $K_2CO_3.1.5H_2O$. The pellets were heated, and then further treated by soaking with 20 ml of an aqueous (deionized $H_2O$) solution containing 0.79 g (3.32 mM) $CoCl_2.6H_2O$. The mole ratio of $K_2CO_3$:$CoCl_2$ was 1. The resulting impregnated pellets were calcined in air at 230° C. for 17 hours. The pellets were cooled and washed with deionized water continuously for 7 hours and then dried.

The catalyst was evaluated by contacting with a gaseous feed containing CO, $C_3H_6$, $O_2$, $N_2$ and He in a reaction zone at various temperatures. The contact time was about 6.2 seconds in each run.

| Temperature (°C.) | Mole % CO In Feed | Mole % CO In Outlet Gas | % CO Conversion |
|---|---|---|---|
| 100 | 0.21 | 0.13 | 38 |
| 120 | 0.24 | 0.02 | 91 |
| 140 | 0.22 | 0.04 | 82 |
| 150 | 0.18 | N.D. | 100 |
| 160 | 0.22 | N.D. | 100 |
| 170 | 0.23 | N.D. | 100 |
| 180 | 0.23 | N.D. | 100 |
| 220 | 0.20 | N.D. | 100 |

N.D. = None Detected

The results clearly show that the catalyst completely and selectively oxidizes CO at temperatures of from about 150° C. to about 220° C. (see FIG. 1). The propylene content in the feed ranged from 2.54 to 2.59 mole percent. No significant oxidation of the propylene was detected.

EXAMPLE 5

Example 4 was repeated except that the amount of $K_2CO_3.1.5H_2O$ and $CoCl_2.6H_2O$ were 1.10 g (6.64 mM), and 1.58 g (6.66 mM), respectively. The mole ratio of $K_2CO_3$:$CoCl_2$ was 1.

| Temperature (°C.) | Mole % CO In Feed | Mole % CO In Outlet Gas | % CO Conversion |
|---|---|---|---|
| 100 | 0.21 | 0.13 | 38 |
| 120 | 0.24 | N.D. | 100 |
| 140 | 0.22 | 0.02 | 91 |
| 150 | 0.18 | N.D. | 100 |
| 160 | 0.22 | N.D. | 100 |
| 170 | 0.23 | N.D. | 100 |
| 180 | 0.23 | N.D. | 100 |
| 220 | 0.20 | N.D. | 100 |

N.D. = None Detected

Figure 2:
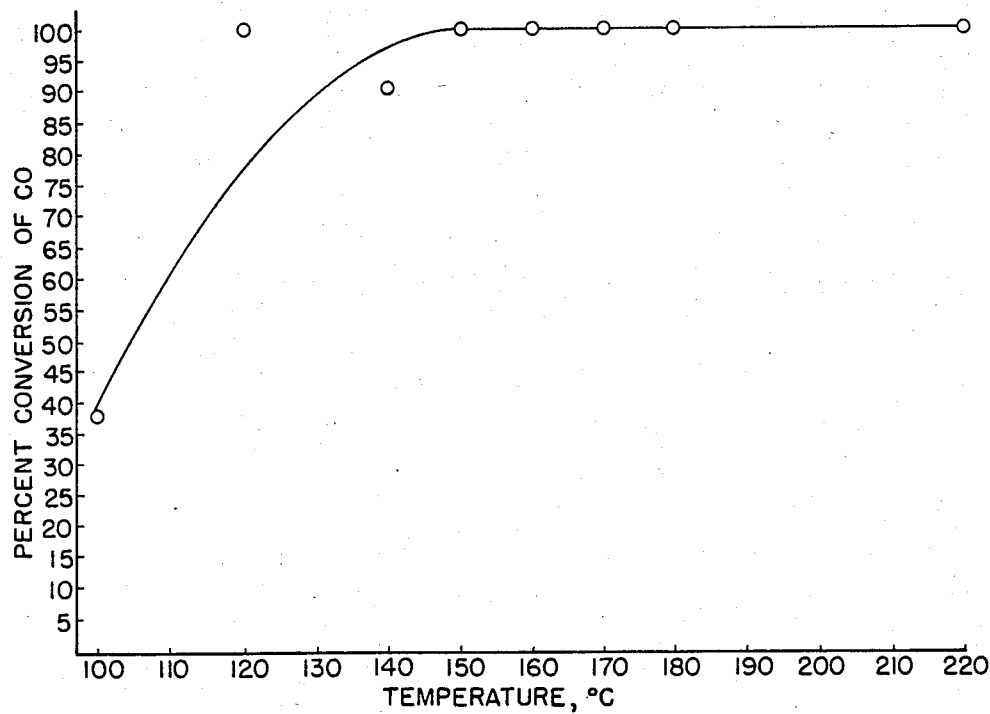

No appreciable oxidation of propylene was observed. Although the amounts of $K_2CO_3.1.5H_2O$ and $CoCl_2.6H_2O$ were doubled compared to Example 4, the mole ratio of $K_2CO_3$:$CoCl_2$ remained 1. The results indicate that the catalyst completely and selectively oxidizes CO at temperatures of from about 150° C. to about 220° C. (see FIG. 2).

EXAMPLE 6

Example 4 was repeated except that the amounts of $K_2CO_3.1\frac{1}{2}H_2O$ and $CoCl_2.6H_2O$ were 0.98 g (6 mM) and 0.40 g (1.68 mM), respectively, to provide a mole ratio of $K_2CO_3$:$CoCl_2$ of 3.6.

| Temperature (°C.) | Mole % CO In Feed | Mole % CO In Outlet Gas | % CO Conversion |
|---|---|---|---|
| 100 | 0.21 | 0.09 | 57 |
| 120 | 0.24 | N.D. | 100 |
| 140 | 0.22 | N.D. | 100 |

N.D. = None Detected

Figure 3:
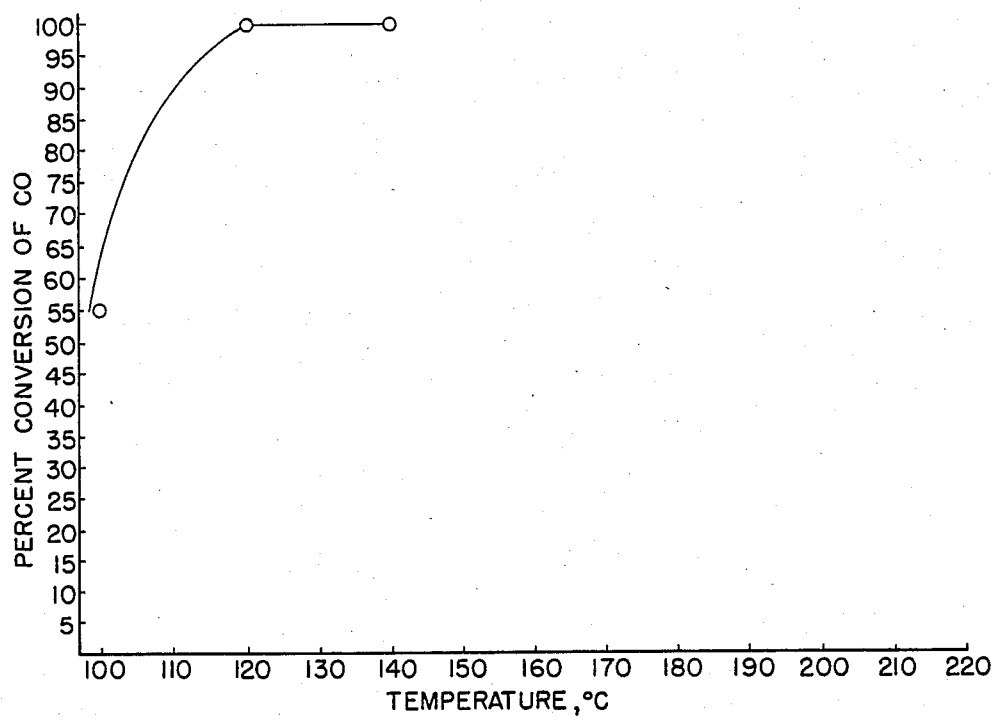

No measurable loss of propylene was detected. The data indicates that using a stoichiometric excess of $K_2CO_3.1\frac{1}{2}H_2O$ provides excellent results especially at lower reaction temperatures (see FIG. 3).

EXAMPLE 7

Example 4 was repeated except that the amounts of $K_2CO_3.1\frac{1}{2}H_2O$ and $CoCl_2.6H_2O$ were 0.98 g (6 mM) and 0.79 g (3.32 mM), respectively, to provide a mole ratio of $K_2CO_3$:$CoCl_2$ of 1.8.

| Temperature (°C.) | Mole % CO In Feed | Mole % CO In Outlet Gas | % CO Conversion |
|---|---|---|---|
| 100 | 0.21 | N.D. | 100 |
| 130 | 0.24 | N.D. | 100 |
| 140 | 0.22 | N.D. | 100 |

No measurable loss of propylene was detected.

Figure 4:
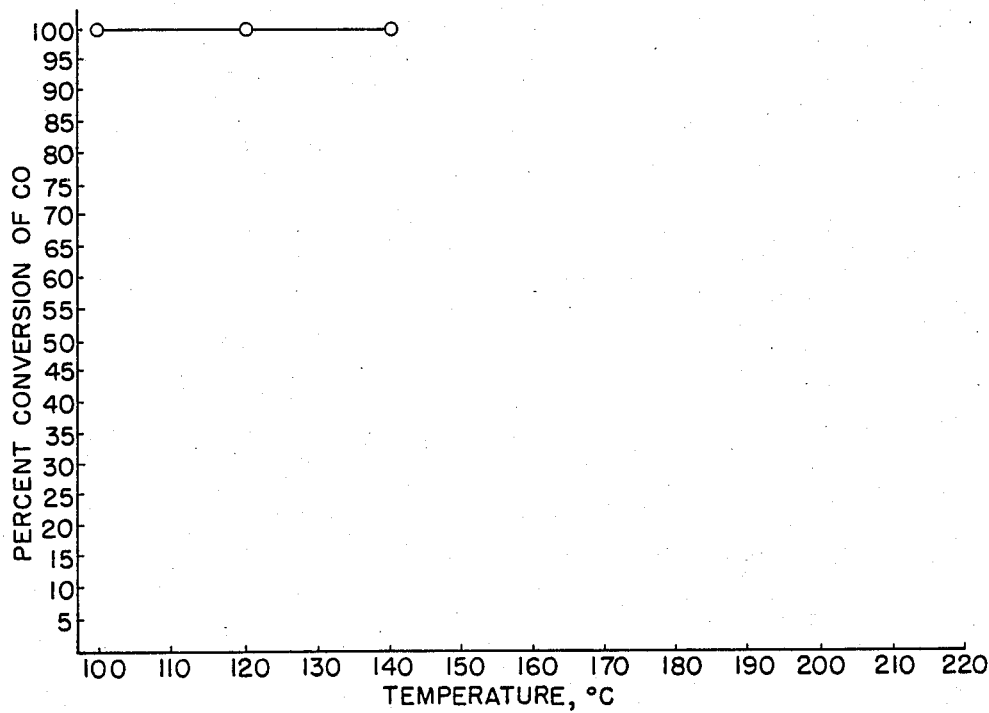

This data confirms the results shown in Example 6 that using a molar ratio of $K_2CO_3$:$CoCl_2$ of greater than 1 provides complete oxidation of CO at low temperatures without oxidizing any of the propylene (see FIG. 4).

It will be apparent that many changes and modifications of the several features described herein may be made without departing from the spirit and scope of the invention. It is, therefore, apparent that the foregoing description is by way of illustration of the invention rather than limitation of the invention.

What is claimed is:

1. A method of preparing, from an alkaline compound and a cobalt compound, an alumina supported cobalt oxide catalyst useful for the selective oxidation of CO in a gaseous reaction medium containing a hydrocarbon which consists essentially of:
   (a) impregnating an alumina support with an aqueous solution of a first water soluble alkaline compound whose anion is capable of forming a water insoluble cobalt compound when said first water soluble alkaline compound is reacted with a water soluble cobalt compound, said water insoluble cobalt compound capable of providing a water insoluble cobalt oxide upon calcination, (b) drying the alkaline compound impregnated alumina support, (c) impregnating the dried alkaline compound impregnated alumina support with an aqueous solution of a water soluble cobalt compound whose anion is capable of forming a second water soluble alkaline compound upon reaction of said first water soluble alkaline compound with said water soluble cobalt compound, whereby an insoluble cobalt compound forms on the support, (d) calcining the cobalt compound impregnated, alkaline compound containing, alumina support to form an insoluble cobalt oxide on the cobalt compound impregnated, alkaline compound containing, alumina support, (e) washing the calcined support with water to remove soluble compounds and activate the cobalt oxide catalyst.

2. A method according to claim 1 wherein the first water soluble alkaline compound contains an alkali or alkaline earth metal cation and a hydroxide or a carbonate anion and the water soluble cobalt compound contains a chloride, a nitrate or a sulfate anion.

3. A method according to claim 2 wherein the first alkaline compound is potassium carbonate, and the cobalt compound is cobaltous chloride.

4. A method according to claim 1 wherein the water used to wash the calcined support is deionized.

5. A method according to claim 1 wherein the molar ratio of the first soluble alkaline compound to the soluble cobalt compound is at least the stoichiometric requirement.

6. A method according to claim 5 wherein the molar ratio is about the stoichiometric requirement to about 5 times the stoichiometric requirement.

7. A method according to claim 1 wherein, in step (d) the impregnated support in step (c) is calcined at about 200° C. to 800° C. for up to about 48 hours.

8. A method according to claim 1 wherein, at the conclusion of step (e), the amount of cobalt on the support, calculated as CoO, is about 0.1% to about 10% by weight of the support.

9. A method according to claim 1 wherein, at the conclusion of step (e), the amount of cobalt on the support, calculated as CoO, is about 0.5% to about 5% by weight of the support.

* * * * *